United States Patent [19]

Feiring

[11] Patent Number: 4,650,913
[45] Date of Patent: Mar. 17, 1987

[54] SULFINATE-INITIATED ADDITION OF PERFLUORINATED IODIDES TO OLEFINS

[75] Inventor: Andrew E. Feiring, Wilmington, Del.

[73] Assignee: E. I. De Pont de Nemours and Company, Wilmington, Del.

[21] Appl. No.: 676,100

[22] Filed: Nov. 29, 1984

[51] Int. Cl.$^4$ ............ C07C 17/28; C07C 101/30
[52] U.S. Cl. .................. 570/144; 570/172; 568/28; 568/35; 560/227; 560/111; 560/197
[58] Field of Search ............ 570/172, 144; 568/28, 568/35; 560/227, 111, 197

[56] References Cited

U.S. PATENT DOCUMENTS

| | | | |
|---|---|---|---|
| 3,535,393 | 10/1970 | Blochl | 570/172 |
| 4,049,718 | 9/1977 | Chabardes et al. | 568/31 |
| 4,058,573 | 11/1977 | Knell | 260/653.1 T |
| 4,073,817 | 2/1978 | Jayer | 570/172 |
| 4,144,244 | 3/1979 | Brace | 260/326 C |
| 4,346,141 | 8/1982 | Remington | 428/289 |
| 4,371,710 | 2/1983 | Umemoto | 568/35 |
| 4,387,254 | 6/1983 | Commeyras et al. | 568/842 |
| 4,394,225 | 7/1983 | Commeyras et al. | 204/59 |
| 4,478,760 | 10/1984 | Blancou et al. | 570/172 |

FOREIGN PATENT DOCUMENTS

| | | |
|---|---|---|
| 0043758 | 1/1982 | European Pat. Off. |
| 0043757 | 1/1982 | European Pat. Off. |
| 3338299 | 2/1985 | Fed. Rep. of Germany |
| 3338300 | 2/1985 | Fed. Rep. of Germany |
| 2516920 | 5/1983 | France |
| 57-085327 | 5/1982 | Japan |
| 1319898 | 6/1973 | United Kingdom |

OTHER PUBLICATIONS

Sheppard et al., *Organic Fluorine Chemistry* (W.A. Benjamin, Inc., New York) (1969) pp. 189–194 and Table 6–1.
Moore, *J. Chem. Eng. Data*, 9:251–254 (1964).
Kondratenko et al., *J. Org. Chem.*, 13:2086–2087 (1977).
Burton et al., *Tet.Letters*, 42:5163–5168 (1966).
Brace, *J. Org. Chem.*, 44:212–217 (1979).
Feiring, *J. Fluorine Chem.*, 24:191–203 (1984).
Feiring, *6th Winter Fluorine Conference*, Daytona Beach, Fla., Feb. (1983).
Feiring, *J. Org. Chem.*, 48:347–354 (1983).

*Primary Examiner*—Natalie Trousof
*Assistant Examiner*—Joseph A. Boska

[57] ABSTRACT

Reaction of a perfluorinated iodide with an olefin initiated by a sulfinate salt to prepare fluorinated iodide and diiodide monomers and surface active agents.

34 Claims, No Drawings

SULFINATE-INITIATED ADDITION OF PERFLUORINATED IODIDES TO OLEFINS

BACKGROUND OF THE INVENTION

This invention concerns the sulfinate-initiated addition of a fluorine-containing iodide to an olefin.

Several types of reactions are known in the art for addition of a fluorine-containing iodide to an olefin. For instance, see in this regard: Sheppard et al., "Organic Fluorine Chemistry", Benjamin, New York, 1969, pages 189 to 194 and Table 6-1. Other representative reactions are summarized hereafter:

Moore, J. Chem. Eng. Data 9, 251 to 254 (1964), UV irradiation;
EPA 43,758, electrochemical initiation;
EPA 43,757, mercuric salt catalysis;
U.S. Pat. No. 4,058,573; U.S. Pat. No. 4,144,244; U.S. Pat. No. 4,436,141; free-radical initiation employing azo compounds and peroxides;
U.K. No. 1,319,898; Burton et al., Tet. Letters 5163 (1966); and Brace, J. Org. Chem. 44, 212 (1979); metallic compounds and/or amines; and
Feiring, J. Fluorine Chem. 24, pages 191 to 203 (1984), addition of perfluoroalkyl iodides to norbornene in the presence of nitronate ions and thiolate ions with concurrent formation of major amounts of side products.

Japanese Application 57-085327 discloses addition of pentafluoro-3-iodopropene to ethylene under ultraviolet irradiation to form 1,1,2,3,3-pentafluoro-5-iodopent-1-ene.

In contrast to the methods practiced by the prior art, the sulfinate-initiated process of this invention can generally be run at lower temperatures, for shorter times, usually forming the desired product in good yield. The process can be scaled up simply, and expensive equipment such as high pressure, UV, and electrochemical equipment is not needed. This process also avoids the need for toxic, explosive, or corrosive initiators such as peroxides, azo compounds and transition metal salts.

Finally, Kondratenko et al., J. Org. Chem. 13, 2086 (1977) disclose that aromatic sulfinic acids react with perfluoroalkyl iodides in liquid ammonia under UV irradiation to give aromatic perfluoroalkyl sulfones. No mention is made of conducting the reaction in the presence of olefins to make fluorinated iodides.

SUMMARY OF THE INVENTION

This invention concerns a method for making a fluorinated iodide of the formula

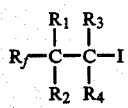

comprising reacting an iodide, $(I)_m R_f$, with an olefin of the formula

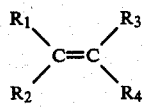

in the presence of a sulfinate salt initiator of the formula $R_5SO_2M$, wherein:

$R_f$ is a perfluorinated primary or secondary $C_1$ to $C_{18}$ moiety which can be aliphatic or alicyclic, can be substituted, or, except for the $C_1$ moiety, internally interrupted by any group that will not react with the sulfinate salt;

$R_1$ to $R_4$ are, individually, H or a substituted or unsubstituted $C_1$ to $C_{16}$ moiety, or $R_1$ to $R_4$, taken together, form a mono- or bicyclic aliphatic ring, the atoms directly linked to olefinic carbon atoms being aliphatic or alicyclic carbon;

$R_5$ is substituted or unsubstituted $C_1$ to $C_{18}$ moiety;

m is 1 or 2; and

M is a cation selected from alkali metal, ammonium, quaternary ammonium or tris(dialkylamino)sulfonium.

DETAILS OF THE INVENTION

The $(I)_m R_f$ starting reactant can be linear, branched or cyclic perfluorinated $C_1$ to $C_{18}$ and contains at least one iodine atom bonded to a carbon which is, in turn, bonded to at least one fluorine. The $C_1$ to $C_{18}$ moiety, which can be aliphatic or alicyclic, can be subsituted, or, except for the $C_1$ moiety, internally interrupted by any group, for example, by heteroatoms such as ether oxygen, or by keto or carbonyloxy groups, that will not react with the sulfinate salt.

Preferred iodides are (i) primary or secondary perfluoroalkyl iodides of the formula $C_nF_{2n+1}I$ where n is an integer from 1 to 18 and (ii) primary perfluoroalkylene diiodides of the formula $I(CF_2)_nI$. More preferred are primary perfluoroalkyl iodides $C_nF_{2n+1}I$ where n is an even number from 2 to 18. Representative fluorine-containing iodides suitable in the process of this invention are 1-iodoperfluorooctane, 2-iodoperfluoropropane, 2-iodoperfluorononane, 1,4-diiodoperfluorobutane, and perfluoro-1-iodo-3-oxa-4-trifluoromethylpentane.

The olefin reactants can be unsubstituted hydrocarbyl or they can contain functional or nonfunctional substituents that do not react with the sulfinate catalyst, provided an aryl group, heteroatom or functional substituent is not directly attached to an olefinic carbon atom. The $R_1$ to $R_4$ moieties can also contain one or more olefinic groups which, in the presence of sulfinate salt initiator, can add to fluorinated iodide, as, for example, in triallylcitrate or diallylsuccinate. Olefins which are preferred in the invention process include $C_{2-10}$ linear 1-olefins, cis- and trans-2-butene, allyl benzene, allylacetate, allylbenzoate, diallylsuccinate, triallylcitrate, norbornene, norbornadiene, methyl undec-10-enoate, cyclopentene and cyclohexene.

The sulfinate salt initiators, $R_5SO_2M$, are unsubstituted or substituted by groups that are stable under the reaction conditions. Representative sulfinate salts are sodium benzenesulfinate, sodium p-toluenesulfinate, sodium methanesulfinate, sodium p-acetamidobenzenesulfinate, and tris(dialkylamino)-sulfoniumbenzenesulfinate wherein the alkyl group has 1 to 8 carbon atoms; the latter compound attributable to another inventor.

The sulfinate salt initiator can be present in any amount sufficient to initiate the fluorinated iodide-forming reaction. It has been found that fluorinated iodides prepared in the process of the invention from olefins wherein at least $R_1$ and $R_2$ are H, can react further with the sulfinate salt initiator. When the starting olefin is ethylene ($R_1$ to $R_4$ are H), the product iodide, $R_fCH_2CH_2I$, can react with the sulfinate present to give the sulfone $R_fCH_2CH_2SO_2R_5$. With substituted ethylenes wherein at least one of $R_1$ to $R_4$ is H, the initially-formed iodide may eliminate hydrogen iodide to give a perfluorinated olefin, as demonstrated in Example 16. Use of smaller amounts of sulfinate salt initiator and lower reaction temperatures will minimize such secondary reactions.

Preferably, the sulfinate salt is employed in the amount of about 1 to 100 mol % of the starting iodide, more preferably about 10 to 50 mol % of the starting iodide.

When preparation of fluorinated alkyl sulfones of the above formula is desired, at least a stoichiometric amount of sulfinate salt with respect to ethylene or the intermediate fluoro iodide adduct of ethylene should be employed. Reaction conditions are essentially the same as those employed in the preparation of the iodide adducts.

Representative substitutents which can be present in the $R_f$ and $R_1$ to $R_5$ moieties include cyano, carboalkoxy, alkoxy, aryloxy, carboaryloxy, aroyloxy, acyloxy, halogen other than iodo, carboxy, carboxylate, keto, amido and carboallyloxy.

The process is typically run in a solvent such as dimethylformamide (DMF), dimethylsulfoxide (DMSO), and acetonitrile. Other solvents inert to the process conditions can be employed, but the process may be somewhat slower. Representative of such other solvents are the hydrocarbons including benzene.

The process requires at least a stoichiometric amount of the olefin relative to the iodide. Since the iodide is normally the more expensive reactant, it is preferred to use a 2- to 5-fold excess of the olefin to maximize the yield of product based on the iodide. The process is operated at temperatures from about 0° C. to 100° C. The preferred temperature range is 10° to 50° C. The reagents and the sulfinate salt can be mixed in any order.

Ambient pressures are preferred because of convenience, but either subatmospheric or superatmospheric pressures can be employed. Either a closed or open reaction vessel can be used. It is preferred to maintain an inert atmosphere of nitrogen or argon during the reaction. When the reaction temperature is above the boiling point of any of the reagents it is preferred to use a closed vessel to minimize loss of the volatile reagent.

The product can be isolated by a variety of techniques. If a water-insoluble solvent is employed, the reaction mixture can be washed with water to remove the sulfinate salt initiator. The product can be recovered by evaporation of the solvent and purification by standard techniques such as distillation, chromatography, and the like. When the preferred water-soluble solvents DMF, DMSO, or acetonitrile are employed the reaction mixture can be treated with an excess of water and the product recovered by extraction with a water-insoluble solvent such as ether or methylene chloride. The product is isolated from the extraction solvent as described above.

Fluorinated iodides prepared by the process of this invention are useful reagents for the preparation of monomers and surface active agents. Examples of this utility are disclosed in U.S. Pat. No. 3,786,089, and U.S. Pat. No. 3,773,826 where fluorine-containing iodides are converted to polymerizable compositions. Other utilities are disclosed in U.S. Pat. No. 4,346,141. The use of compounds made by this process as synthetic intermediates is described by Brace, J. Fluorine Chem., 20, 313 (1982).

Fluorinated alkyl sulfones prepared by the process of this invention are useful as oil and waterproofing agents for textiles and papers, and as industrial and/or biological transporters of dissolved gases. Related utilities are disclosed in German Patent No. 2,052,579 and in French Patent No. 2,516,920; the latter discloses use of perfluoroalkyl sulfones as blood substitutes.

The following Examples illustrate the process of this invention. Temperatures are in degrees Celsius.

EXAMPLE 1

A mixture of 6.0 g (0.03 mole) of sodium benzenesulfinate dihydrate, 100 mL of dimethylformamide (DMF) which had been bubbled with argon to remove oxygen, 9.4 g (0.1 mole) of norbornene and 10.9 g (0.02 mole) of perfluorooctyl iodide was stirred overnight. The mixture was poured into 300 mL of ether and 300 mL of water. The ether solution was washed with $3 \times 100$ mL of water and dried over anhydrous magnesium sulfate. Glpc (gas-liquid partition chromatography) analysis using a 1.83 m by 0.32 cm 10% methyl silicone fluid (SP-2100; Supelco) column with helium carrier gas flow rate of 40 mL/min and an oven temperature of 70° for 2 min (then heated from 70° to 230° at 16°/min) revealed the absence of a peak due to unreacted perfluorooctyl iodide and the presence of a new peak with the retention time of 9.5 minutes. The ether solution was concentrated on a rotary evaporator giving 11.9 g (93%) of 2-iodo-3-perfluorooctylnorbornane, proton NMR ($\delta$ CDCl3/TMS) 1.1–2.8 (9H,m); 4.32 (1H,m), fluorine NMR ($\delta$ CDCl3/CFCl3) —81.55 (3F); —126.74 (2F); —123.21 (2F); —122.30 (6F); —121.25 (2F); —117.69 (2F, AB quartet, Jab=280 Hz).

EXAMPLE 2

A mixture of 3.6 g (0.02 mole) of sodium p-toluenesulfinate and 100 mL of DMF was heated under argon to 60° then cooled to room temperature to give a saturated solution. Norbornene (4.7 g, 0.05 mole) and perfluorooctyl iodide (10.9 g, 0.02 mole) were added and the mixture was stirred overnight at room temperature. The mixture was poured into 300 mL of ether and 300 mL of water. The ether solution was washed with $3 \times 100$ mL of water and dried over anhydrous magnesium sulfate. Glpc analysis as in Example 1 showed a peak for 2-iodo-3-perfluorooctylnorbornane and no peak for unreacted perfluorooctyl iodide. The ether solution was concentrated on a rotary evaporator to 12.0 g (94%) of product as an oil which crystallized on standing.

EXAMPLE 3

A solution of 10.9 g (0.02 mole) of perfluorooctyl iodide, 90 mL of DMF, and 9.4 g (0.1 mole) of norbornene was partially evacuated and filled with argon to remove oxygen. Sodium methanesulfinate (2.1 g, 0.021 mole) was added and the mixture was stirred overnight. The mixture was added to 300 mL of ether and 300 mL of water. The separated ether solution was washed with $3 \times 100$ mL of water and dried over anhydrous magnesium sulfate. Glpc analysis as in Example 1 showed a peak corresponding to 2-iodo-3-perfluorooctylnorbornane and no unreacted perfluorooctyl iodide. The ether solution was concentrated on a rotary evaporator to an oil. Kugelrohr distillation of the oil at 0.1 mm pressure and a heating bath temperature of 95° gave 10.7 g (84%) of product as a colorless liquid which crystallized to a white solid.

EXAMPLE 4

A mixture of 10.9 g (0.02 mole) of perfluorooctyl iodide, 9.4 g (0.01 mole) of norbornene, 100 mL of DMF and 2.2 g (0.01 mole) of sodium p-acetamidobenzenesulfinate was stirred overnight at room temperature under argon. Work-up as in Example 1 afforded 12.5 g of crude product. Kugelrohr distillation at 0.15 mm pressure and a bath temperature of up to 100° gave 10.8 g (84%) of 2-iodo-3-perfluorooctylnorbornane.

EXAMPLE 5

A 50 mL portion of a DMF solution which was 0.5 Molar in norbornene and 0.2 Molar in perfluorooctyl iodide was treated with 0.2 g (0.0012 mole) of sodium p-toluenesulfinate. The solution was stirred overnight. The solution was added to 200 mL of ether and 200 mL of water. The separated ether solution was washed with 3×100 mL of water and dried over anhydrous magnesium sulfate. Glpc analysis as in Example 1 showed the formation of 2-iodo-3-perfluorooctylnorbornane with no unreacted perfluorooctyl iodide remaining in the solution. Concentration of the solution on a rotary evaporator gave 5.75 g (90%) of product.

EXAMPLE 6

A solution of 0.9 g (0.005 mole) of sodium p-toluenesulfinate in 100 mL of DMF was evacuated and filled with argon several times. Norbornene (9.4 g, 0.1 mole) was added, followed by 10.9 g (0.02 mole) of perfluorooctyl iodide. At one hour intervals after the addition of the perfluorooctyl iodide, 5 mL aliquots of the solution were removed by syringe and injected into 15 mL of ether and 15 mL of water. The ether solution was washed with 3×15 mL of water and dried over anhydrous magnesium sulfate. The ether solution was analyzed by glpc, according to the conditions of Example 1, for the presence of 2-iodo-3-perfluorooctylnorbornane and unreacted perfluorooctyl iodide. After 4 hours reaction time, this analysis showed a complete disappearance of the perfluorooctyl iodide. The remaining solution was poured into 300 mL of ether and 300 mL of water. The ether solution was washed with 3×100 mL of water, dried over anhydrous magnesium sulfate, and concentrated on a rotary evaporator to an oil. Kugelrohr distillation of this oil at 0.25 mm pressure and a bath temperature of up to 100° gave 7.7 g of product as an oil which crystallized on standing.

EXAMPLE 7

A mixture of 3.6 g (0.02 mole) of sodium p-toluenesulfinate, 9.4 g (0.1 mole) of norbornene, 10.9 g (0.02 mole) of perfluorooctyl iodide, and 90 mL of dimethylsulfoxide (DMSO) which had been bubbled with argon to remove oxygen was stirred overnight. The mixture was then subjected to the work-up procedure given in Example 1. Kugelrohr distillation of the crude product at 0.25 mm pressure and a bath temperature of up to 126° gave 10.41 g (81%) of 2-iodo-3-perfluorooctylnorbornane as an oil which crystallized on standing.

EXAMPLE 8

The procedure of Example 7 was followed using 90 mL of acetonitrile in place of DMSO. This afforded 10.79 g (84%) of 2-iodo-3-perfluorooctylnorbornane.

EXAMPLE 9

The procedure of Example 7 was followed using 100 mL of benzene in place of DMSO. The reaction mixture was washed with 3×100 mL of water and dried over anhydrous magnesium sulfate. Glpc analysis of the benzene solution according to the procedure of Example 1 showed the presence of two peaks after peaks for solvent and excess norbornene:

| Peak | Retention Time | Area % |
| --- | --- | --- |
| 1 | 1.94 min | 84.1 |
| 2 | 9.65 min | 15.6 |

The first peak corresponds to unreacted perfluorooctyl iodide; the second to 2-iodo-3-perfluoroocytlnorbornane. The benzene solution was concentrated on the rotary evaporator and evacuated to 0.25 mm pressure giving 2.46 g (19%) of product. This Example demonstrates that the reaction proceeds in a nonpolar solvent such as benzene, but is slower compared to reactions in dipolar solvents such as DMF, DMSO, or acetonitrile.

EXAMPLE 10

A mixture of 3.6 g (0.02 mole) of sodium p-toluenesulfinate, 100 mL of DMF and 9.4 g (0.1 mole) of norbornene was partially evacuated and filled with argon to remove oxygen; then, 2-iodoperfluoropropane (5.9 g, 0.02 mole) was added. The mixture was stirred overnight and then poured into 300 mL of ether and 300 mL of water. The separated ether solution was washed with 3×100 mL of water and dried over anhydrous magnesium sulfate. Evaporation of the ether on a rotary evaporator gave 5.4 g of oil. Kugelrohr distillation of the oil at 23 mm pressure and a bath temperature up to 130° gave 4.54 g (58%) of 2-iodo-3-(2-perfluoropropyl)-norbornane.

EXAMPLE 11

A mixture of 4.7 g (0.05 mole) of norbornene, 5.9 g (0.01 mole) of 2-iodoperfluorononane, 50 mL of DMF, and 1.8 g (0.01 mole) of sodium p-toluenesulfinate was partially evacuated and filled with argon several times to remove oxygen. The mixture was stirred overnight at room temperature. The mixture was poured into 150 mL of ether and 150 mL of water. The separated ether solution was washed with 3×50 mL of water and dried over anhydrous magnesium sulfate. Glpc analysis of the ether solution as in Example 1 showed no peak for unreacted 2-iodoperfluorononane. The analysis showed the presence of two closely spaced peaks with retention times of b 9.5 and 9.6 minutes. The ether solution was concentrated on the rotary evaporator. The residual oil was distilled in a Kugelrohr apparatus at 0.25 mm pressure and a bath temperature of up to 113° giving 5.0 g (85%) of colorless oil. The product structure was assigned as a 1:1 mixture of diastereomers of 2-iodo-3-(2-perfluorononyl)norbornane on the basis of proton and fluorine NMR spectra.

EXAMPLE 12

A mixture of 9.4 g (0.1 mole) of norbornene, 100 mL of DMF, 9.1 g (0.02 mole) of 1,4-diiodoperfluorobutane, and 1.8 g (0.01 mole) of sodium p-toluenesulfinate was stirred overnight at room temperature. The mixture was poured into 300 mL of ether and 300 mL of water. The separated ether layer was washed with 3×100 mL of water and dried over anhydrous magnesium sulfate. The solution was concentrated on the rotary evaporator leaving 12.21 g of off-white solid. The solid was dissolved in 100 mL of ether. Silica gel (30 g) was added and the solvent was evaporated on the rotary evaporator. This material was added to the top of a column of 300 g of silica gel packed in hexane. The column was eluted with hexane, taking 100 mL fractions. Fractions 12 to 25 were combined and concentrated on a rotary evaporator to 10.6 g (83%) of white solid, mp 114°–115°. This material was identified as the 2:1 adduct of norbornene:diiodide by NMR.

EXAMPLE 13

A mixture of 3.8 g (0.021 mole) of sodium p-toluenesulfinate, 4.7 g (0.05 mole) of norbornene and 100 mL of DMF was partially evacuated and filled with argon to remove oxygen. Perfluoro-1-iodo-3-oxa-4-trifluoromethylpentane (8.2 g, 0.02 mole) was added and the mixture was stirred overnight. The mixture was poured into 300 mL of ether and 300 mL of water. The separated ether solution was washed with 3×100 mL of water and dried over anhydrous magnesium sulfate. The ether solution was concentrated on a rotary evaporator to 7.9 g of colorless liquid. Kugelrohr distillation of the oil at 0.35 mm and a bath temperature of up to 100° gave 5.97 g (59%) of 2-iodo-3-(perfluoro-3-oxa-4-trifluoromethylpentyl)norbornane as identified by proton and fluorine NMR.

EXAMPLE 14

A mixture of 100 mL of DMF which was bubbled with argon to remove oxygen, 10.9 g (0.02 mole) of perfluorooctyl iodide, 4.1 g (0.06 mole) of cyclopentene, and 1.8 g (0.01 mole) of sodium p-toluenesulfinate was stirred overnight at room temperature. The mixture was poured into 300 mL of ether and 300 mL of water. The ether solution was washed with 3×100 mL of water and dried over anhydrous magnesium sulfate. Glpc analysis, according to the procedure of Example 1, for the ether solution showed three peaks after the solvent peak:

| Peak | Retention Time | Area % |
| --- | --- | --- |
| 1 | 1.71 min | 33.4 |
| 2 | 4.86 min | 3.3 |
| 3 | 7.94 min | 63.0 |

The first peak had the retention time of perfluorooctyl iodide. The ether solution was concentrated on the rotary evaporator to 10.5 g of oil. Kugelrohr distillation of the oil at 0.5 mm pressure and a bath temperature of up to 100° gave 5.6 g of light orange oil which was 94.3% peak 3 material by glpc analysis. This material was identified as 1-iodo-2-perfluorooctylcyclopentane by NMR. The proton NMR showed multiplets at 1.6–2.5 (6H), 3.20 (1H), and 4.53 (1H).

EXAMPLE 15

A nitrogen-swept 200 mL pressure vessel was charged with 3.6 g (0.02 mole) of sodium p-toluenesulfinate, 90 mL of DMF and 10.9 g (0.02 mole) of perfluorooctyl iodide. The vessel was closed, cooled in dry ice/acetone and evacuated. Excess propene (15 g) was condensed into the vessel. The vessel was agitated overnight with the contents at room temperature. The vessel was vented to 1 atm pressure and the contents were poured out. The vessel was rinsed with 50 mL of DMF. The combined DMF solutions were added to 300 mL of ether and 300 mL of water. The separated ether layer was washed with 3×100 mL of water and dried over anhydrous magnesium sulfate. Glpc analysis of the ether solution according to the conditions of Example 1 showed the presence of two peaks after solvent peak:

| Peak | Retention Time | Area % |
| --- | --- | --- |
| 1 | 1.95 min | 43.6 |
| 2 | 5.80 min | 45.1 |

The ether solution was concentrated on the rotary evaporator to 9.6 g of solid. NMR confirmed the formation of the addition product of the perfluorooctyl iodide to propene. The product was further purified by chromatography over 300 g of silica gel. The column was eluted with hexane taking 100 mL fractions. Fractions 6 to 11 were combined and concentrated on a rotary evaporator. The residue was Kugelrohr-distilled at 25 mm pressure and a bath temperature of up to 95° giving 4.04 g (34%) of 2-iodi-1-perfluorooctylpropane as a faintly yellow solid.

EXAMPLE 16

A mixture of 10.9 g (0.02 mole) of perfluorooctyl iodide, 12 mL (0.077 mole) of 1-octene, 100 mL of DMF, and 3.6 g (0.02 mole) of sodium p-toluenesulfinate was stirred overnight at room temperature under argon. The mixture was poured into 300 mL of ether and 300 mL of water. The ether solution was washed with 3×100 mL of water and dried over anhydrous magnesium sulfate. Glpc analysis of the ether solution according to the procedure of Example 1 showed three peaks after the peaks for solvent and excess octen:

| Peak | Retention Time | Area % |
| --- | --- | --- |
| 1 | 1.66 min | 9.2 |
| 2 | 7.16 min | 21.1 |
| 3 | 9.60 min | 63.8 |

The first peak is unreacted perfluorooctyl iodide. The third peak is assigned to the adduct of the iodide to octene and the second peak is assigned to the HI elimination product from this adduct.

The ether solution was concentrated on the rotary evaporator giving 15.2 g of oil. The oil was Kugelrohr distilled at 0.25 mm pressure and a bath temperature of up to 120°. The distillate was dissolved in 100 mL of methanol and the solution was added to a solution of 5 g of potassium hydroxide pellets in 100 mL of methanol. The solution was stirred for 1 hr at room temperature. The solution was poured into 300 mL of ice water containing 20 mL of concentrated hydrochloric acid. This was extracted with 3×100 mL of 1,1,2-tricholotrifluoroethane. The combined extracts were washed with 2×100 mL of water and dried over anhydrous magnesium sulfate. Glpc analysis as above showed only the peak at 7.16 min. The solution was concentrated on the rotary evaporator to 7.7 g (73%) of colorless liquid. The structure of this material was assigned as 1,1,1,2,2,3,3,4,4,5,5,6,6,7,7,8,8-heptadecafluorohexadec-9-ene on the basis of its NMR spectrum.

EXAMPLE 17

The procedure of Example 16 was followed using 11.2 g (0.1 mole) of 1-octene and 0.9 g (0.005 mole) of sodium p-toluenesulfinate. Glpc analysis of the ether solution showed the following peaks:

| Peak | Area % |
| --- | --- |
| 1 | 17.9 |
| 2 | 5.4 |
| 3 | 72.7 |

This Example demonstrates that more of the 1:1 adduct (peak 3) is obtained relative to the HI elimination product (peak 2) when less of the initiator is employed. The ether solution was concentrated on the rotary evaporator to 13.02 g of oil. Kugelrohr distillation of the oil at 0.35 mm pressure and a bath temperature of up to 180° gave 9.3 g (71%) of liquid, identified as 1,1,1,2,2,3,3,4,4,5,5,6,6,7,7,8,8,heptadecafluoro-10-iodohexadecane by its NMR spectra.

EXAMPLE 18

The procedure of Example 17 was followed using 8.0 g (0.08 mole) of allyl acetate in place of the 1-octene. Kugelrohr distillation of the product at 0.4 mm pressure and a bath temperature of up to 90° gave 3.7 g (29%) of 4,4,5,5,6,6,7,7,8,8,9,9,10,-10,11,11,11-heptadecafluoro-2-iodoundecenyl acetate as indicated by the proton NMR spectrum.

EXAMPLE 19

The procedure of Example 17 was followed using 4.7 g (0.04 mole) of allylbenzene in place of the 1-octene. Concentration of the ether solution on a rotary evaporator gave 13.8 g of oil. The oil was chromatographed on 300 g of silica gel. The column was eluted with 1 L of hexane and 1 L of 10% ether in hexane, taking 100 mL fractions. From fractions 14 to 17 was isolated 0.41 g of pure 4,4,5,5,6,6,7,7,-8,8,9,9,10,10,11,11,11-heptadecafluoro-2-iodo-1-phenylundecane as identified by fluorine and proton NMR. Kugelrohr distillation of the material from fractions 9 to 13 and 18 at 0.15 mm and a bath temperature of up to 106° gave an additional 0.86 g of slightly less pure product.

EXAMPLE 20

The procedure of Example 17 was followed using 4.1 g (0.021 mole) of methyl undec-10-eneoate in place of the 1-octene, 60 mL of DMF and a 66 hr reaction time. Glpc analysis of the ether solution according to the procedure of Example 1 showed five peaks after the solvent peak.

| Peak | Retention Time | Area % |
| --- | --- | --- |
| 1 | 1.75 min | 7.1 |
| 2 | 8.98 min | 6.4 |
| 3 | 11.57 min | 14.2 |
| 4 | 12.02 min | 14.8 |
| 5 | 14.31 min | 57.0 |

The first two peaks are unreacted perfluorooctyl iodide and methyl undec-10-enoate, respectively. Concentration of the ether solution on a rotary evaporator gave 13.75 g of oil. The oil was chromatographed on 300 g of silica gel packed in hexane. The column was eluted with 1 L hexane and 1L 10% ether/hexane, taking 100 mL fractions. Fractions 17 to 20 were combined and concentrated to 10.9 g of oil which was 61% peak #5 by Glpc analysis. Proton and fluorine NMR confirmed the formation of $C_8F_{17}CH_2CHI(CH_2)_8CO_2CH_3$.

EXAMPLE 21

The reaction of perfluorooctyl iodide, ethylene, and sodium p-toluenesulfinate in DMF was conducted as follows. A nitrogen-swept 200 mL pressure vessel was charged with 3.6 g (0.02 mole) of sodium p-toluenesulfinate, 90 mL of DMF, and 10.9 g (0.02 mole) of perfluorooctyl iodide. The vessel was closed, cooled in dry ice and acetone and evacuated. Ethylene (10 g, 0.42 mole) was condensed in the vessel. The mixture was agitated overnight at room temperature. The vessel was vented to 1 atmosphere pressure and the contents were poured into 300 mL of ether and 300 mL of water. The ether solution was washed with 3×100 mL of water and dried over anhydrous magnesium sulfate. Glpc analysis of the ether solution according to the procedure of Example 1 showed three major peaks after the solvent peak:

| Peak | Retention Time | Area % |
| --- | --- | --- |
| 1 | 1.87 min. | 31.2 |
| 2 | 5.18 min. | 20.0 |
| 3 | 11.77 min. | 34.0 |

The first peak is unreacted perfluorooctyl iodide. The ether solution was concentrated on the rotary evaporator to 10.03 g of oily orange solid. The crude product adsorbed on 30 g of silica gel was added to a column of 300 g of silica gel packed in hexane. The column was eluted with 1 L of hexane, 1 L of 5% ether in hexane, 0.5 L of 10% ether in hexane, 1 L of 25% ether in hexane, and 3 L of 35% ether in hexane, taking 100 mL fractions. From fractions 6 to 9 was isolated 1.92 g (17%) of 1H, 1H, 2H, 2H-perfluorodecyliodide, mp 56° to 57°, as confirmed by proton NMR and by fluorine NMR. From fractions 32 to 58 was isolated 3.94 g (33%) of $C_8F_{17}CH_2CH_2SO_2C_6H_4CH_3$ as a white solid, mp 109° to 111°, as confirmed by proton NMR and by fluorine NMR. Analysis: Calcd. for $C_{17}H_{11}F_{17}SO_2$: C, 33.90; H, 1.84; F, 53.63; S, 5.32. Found: C, 33.83; H, 1.92; F, 53.57; S, 5.49.

I claim:

1. A method for making a fluorinated iodide of the formula

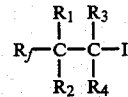

comprising reacting an iodide, $(I)_mR_f$, with an olefin of the formula

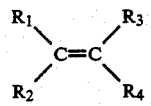

in the presence of a sulfinate salt initiator of the formula $R_5SO_2M$, wherein:

$R_f$ is a perfluorinated primary or secondary $C_1$ to $C_{18}$ moiety which can be aliphatic or alicyclic, can be substituted, or, except for the C₁ moiety, internally interrupted by any groups, provided that said substituent or said internal group will not react with the sulfinate salt;

$R_1$ to $R_4$ are, individually, H or a substituted or unsubstituted $C_1$ to $C_{16}$ moiety, or $R_1$ to $R_4$, taken together, form a mono- or bicyclic aliphatic ring, the atoms directly linked to olefinic carbon atoms being aliphatic or alicyclic carbon;

$R_5$ is a substituted or unsubstituted $C_1$ to $C_{18}$ moiety;

m is 1 or 2; and

M is a cation selected from alkali metal, ammonium, quaternary ammonium or tris(dialkylamino)sulfonium.

2. A method according to claim 1 employing an iodide which is selected from (i) a primary or secondary perfluoroalkyl iodide of the formula $C_nF_{2n+1}I$, and (ii) a primary perfluoroalkylene diiodide of the formula $I(CF_2)_nI$: wherein n is an integer from 1 to 18.

3. A method according to claim 2 wherein the olefin is ethylene.

4. A method according to claim 2 wherein $R_1$ to $R_3$ are each H and $R_4$ is a substituted or unsubstituted $C_1$ to $C_{16}$ moiety which is alkyl or aralkyl.

5. A method according to claim 4 wherein $R_4$ is alkyl containing at least one functional substituent.

6. A method according to claim 5 wherein the substituent is acyloxy or aroyloxy.

7. A method according to claim 2 wherein at least one of $R_1$ to $R_4$ contains one or more olefinic groups capable of adding to the iodide.

8. A method according to claim 2 wherein the olefin is alicyclic.

9. A method according to claim 7 wherein the olefin is a di- or triallyl ester.

10. A method according to claim 2 wherein $R_5$ is phenyl, substituted phenyl, or methyl.

11. A method according to claim 10 wherein M is sodium, tetraalkylammonium, or tris(dimethylamino)sulfonium.

12. A method according to claim 2 wherein the iodide is a primary perfluoralkyl iodide and n is an even number from 2 to 18.

13. A method according to claim 2 wherein the iodide is a secondary perfluoroalkyl iodide.

14. A method according to claim 1 wherein the iodide is a primary perfluoroalkylene diiodide.

15. A method according to claim 2 wherein the iodide is perfluoro-1-iodo-3-oxa-4-trifluoromethylpentane.

16. A method according to claim 12 wherein the iodide is 1-iodoperfluorooctane.

17. A method according to claim 13 wherein the iodide is 2-iodoperfluoropropane.

18. A method according to claim 13 wherein the iodide is 2-iodoperfluorononane.

19. A method according to claim 14 wherein the iodide is 1,4-diiodoperfluorobutane.

20. A method according to claim 8 employing norbornene as the olefin.

21. A method according to claim 8 employing cyclopentene as the olefin.

22. A method according to claim 4 employing propene as the olefin.

23. A method according to claim 4 employing 1-octene as the olefin.

24. A method according to claim 2 employing allyl acetate as the olefin.

25. A method according to claim 2 employing allylbenzene as the olefin.

26. A method according to claim 2 employing methyl undec-10-eneoate as the olefin.

27. A method according to claim 12 employing sodium benzenesulfinate as initiator.

28. A method according to claim 12 employing sodium methanesulfinate as initiator.

29. A method according to claim 12 employing sodium p-acetamidobenzenesulfinate as initiator.

30. A method according to claim 12 employing sodium p-toluenesulfinate as initiator.

31. A method according to claim 1 run in a stoichiometric excess of olefin at a temperature of about 0° C. to 100° C. at atmospheric pressure employing the initiator in an amount of about 10 to 50 mol percent of the starting iodide.

32. A method according to claim 2 run in a stoichiometric excess of olefin at a temperature of about 0° C. to 100° C. atmospheric pressure employing the initiator in an amount of about 10 to 50 ml percent of the starting iodide.

33. A method for making a fluorinated alkyl sulfone of the formula

comprising reacting an iodide of the formula

with ethylene, and at least a stoichiometric amount of sulfinate initiator of the formula $R_5SO_2M$ wherein $R_f$ is a perfluorinated primary or secondary $C_1$ to $C_{18}$ moiety which can be aliphatic or alicyclic, can be substituted, or, except for the C₁ moiety, internally interrupted by any group, provided that said substituent or said internal group will not react with the sulfinate salt;

m is 1 or 2;

$R_5$ is a substituted or unsubstituted $C_1$ to $C_{18}$ moiety; and

M is a cation selected from alkali metal, ammonium, quaternary ammonium or tris(dialkylamino)sulfonium.

34. In a method for making a fluorinated iodide of the formula

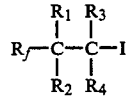

comprising reacting an iodide, $(I)_mR_f$, with an olefin of the formula

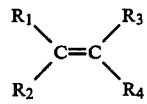

wherein $R_f$ is a perfluorinated primary or secondary $C_1$ to $C_{18}$ moiety which can be aliphatic or alicyclic, can be substituted, or, except for the C₁ moiety, internally interrupted by any group, provided that said substituent or said internal group will not react with the sulfinate salt;

$R_1$ to $R_4$ are, individually, H or a substituted or unsubstituted $C_1$ to $C_{16}$ moiety, or $R_1$ to $R_4$, taken together, form a mono- or bicyclic aliphatic ring, the atoms directly linked to olefinic carbon atoms being aliphatic or alicyclic carbon; and m is 1 or 2;

the improvement comprising conducting the reaction in the presence of a sulfinate salt initiator of the formula $R_5SO_2M$, wherein
- $R_5$ is a substituted or unsubstituted $C_1$ to $C_{18}$ moiety; and
- M is a cation selected from alkali metal, ammonium, quaternary ammonium or tris(dialkylamino)sulfonium.

* * * * *